United States Patent
Miyauchi et al.

(10) Patent No.: US 6,834,207 B2
(45) Date of Patent: Dec. 21, 2004

(54) OPERATING GUIDANCE SYSTEM FOR MEDICAL EQUIPMENT

(75) Inventors: Akihiro Miyauchi, Tochigi-ken (JP); Jun Takahashi, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 153 days.

(21) Appl. No.: 10/067,419

(22) Filed: Feb. 7, 2002

(65) Prior Publication Data

US 2002/0112733 A1 Aug. 22, 2002

(30) Foreign Application Priority Data

Feb. 8, 2001 (JP) .................................... P2001-032770

(51) Int. Cl.[7] .............................................. G05B 19/18
(52) U.S. Cl. ............................ 700/65; 700/83; 700/17; 700/14; 600/300; 434/365; 434/379; 434/401; 345/717; 345/719
(58) Field of Search ........................... 700/65, 83, 2–5, 700/14–17, 20, 75, 76, 84, 264; 600/300; 434/365, 369, 379, 401, 428; 345/704, 727, 716–719; 340/3.1, 3.9, 3.71

(56) References Cited

U.S. PATENT DOCUMENTS

| | | | | |
|---|---|---|---|---|
| 5,445,166 A | * | 8/1995 | Taylor | 128/897 |
| 5,882,206 A | * | 3/1999 | Gillio | 434/262 |
| 5,891,035 A | | 4/1999 | Wood et al. | 600/437 |
| 5,950,629 A | * | 9/1999 | Taylor et al. | 128/897 |
| 6,024,539 A | * | 2/2000 | Blomquist | 417/63 |
| 6,083,163 A | * | 7/2000 | Wegner et al. | 600/429 |
| 6,351,671 B1 | * | 2/2002 | Myklebust et al. | 607/5 |
| 6,386,882 B1 | * | 5/2002 | Linberg | 434/262 |
| 6,409,662 B1 | * | 6/2002 | Lloyd et al. | 600/300 |
| 6,490,490 B1 | * | 12/2002 | Uchikubo et al. | 700/65 |
| 6,522,906 B1 | * | 2/2003 | Salisbury et al. | 600/407 |
| 2001/0037366 A1 | * | 11/2001 | Webb et al. | 709/204 |

* cited by examiner

*Primary Examiner*—Anthony Knight
*Assistant Examiner*—Crystal J Barnes
(74) *Attorney, Agent, or Firm*—Oblon, Spivak, McClelland, Maier & Neustadt, P.C.

(57) ABSTRACT

A remote maintenance and operating guidance system in which data relating to the operation of a medical system in a hospital is transmitted to an operator who operates an operating device of the medical system from a service center by way of a communication device such as a dedicated telephone line. The system is equipped to monitor operations performed by the operator on the medical system, and to transmit data relating to the monitored operation to the operating device. Accordingly, it is possible to transmit details of the method of operation of the medical equipment more accurately and effectively to the operator from a location remote from the medical equipment.

9 Claims, 5 Drawing Sheets

OPERATING GUIDANCE SYSTEM FOR MEDICAL EQUIPMENT

CROSS-REFERENCE TO RELATED APPLICATIONS

This application claims benefit of priority under 35 USC §119 to Japanese Patent Application No. P2001-032770 filed Feb. 8, 2001, the entire contents of which are incorporated by reference herein.

BACKGROUND OF THE INVENTION

Recent years have witnessed the widespread introduction into hospitals and other medical facilities of large-scale imaging modalities including magnetic resonance imaging, X-ray CT scanning, X-ray diagnostic, nuclear medicine imaging, ultrasonic calculus pulverizing, SQUID and ultrasonic diagnostic devices.

These modalities reflect recent advances in electronic and image processing technology, and their operation is becoming increasingly complex. Moreover, they are frequently upgraded by adding new applications to an existing modality. As a result, it has begun to place a considerable burden on both physician and operator to learn how to operate the devices.

The simplest way to learn how to operate a modality of this sort is for the operator himself to read an instruction manual. It is also possible to learn while practicing in advance on a different system. Experienced operators will often use an actual device to teach others how to operate it. Whichever method is adopted, the learner needs to rely on a manual or the advice of an experienced operator whenever he comes across something which he does not understand.

If in such circumstances there is no experienced operator in the hospital, the learner will need to seek advice from the service center of the manufacturer of the medical system, or an acquaintance with experience in operating the device. The service center or acquaintance will normally be physically remote from the operator, and will need to give instructions by telephone or other means of voice communications.

However, there are situations where detailed instructions given by an experienced operator in a remote location or from a service center do not come over accurately to the operator, and this may easily result in trouble. This is particularly true if there is a considerable gap in understanding and degree of experience between the instructing party and the instructed party, and where voice communication is solely used.

SUMMARY OF THE INVENTION

Accordingly, it is an object of the present invention to ameliorate the problems associated with conventional methods of remote instruction, and to provide an operating guidance system for a medical system whereby it is possible to give accurate and effective instruction on the operation of a medical imaging system from a distance.

In order to attain the above object, the operating guidance system for medical equipment to which the present invention pertains is basically structured in such a manner that data relating to the operation of the medical equipment is transmitted to an operator operating the medical equipment in a medical facility from a service facility located at a distance from the medical facility by way of a means of communication.

According to one aspect of the present invention, there is provided a medical system which includes a disk unit which stores a plurality of ways an operator can be guided in an operation of the medical system, a console with which the operator selects at least one of the ways, and a communications device which interchanges data with the service center according to the selected way.

According to another aspect of the present invention, there is provided a medical system which includes a disk unit which stores a plurality of ways an operator can be guided in an operation of the medical system, a selection unit which automatically selects at least one of the ways on the basis of a parameter for selection stored in the disk unit, a monitor control unit displays which the selected way on a monitor of the medical system, a console with which the operator selects at least one of the ways displayed on the monitor, and a communications device which interchanges data with the service center according to the selected way.

According to a further aspect of the present invention, there is provided a server system including a storing unit which stores a plurality of ways an operator can be guided in an operation of the medical system, a data receiving device which receives data according to one of the ways from the medical system, a determination unit which determines a type of the way on the basis of the received data, and a sending device which sends a data according to the determined way.

According to a further aspect of the present invention, there is provided an operating guidance system which includes a disk unit which stores a plurality of ways an operator can be guided in an operation of the medical system, a console with which the operator selects at least one of the ways; and a communications device which interchanges data according to the selected way between the medical system and a server system.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE INVENTION

Figure 1:
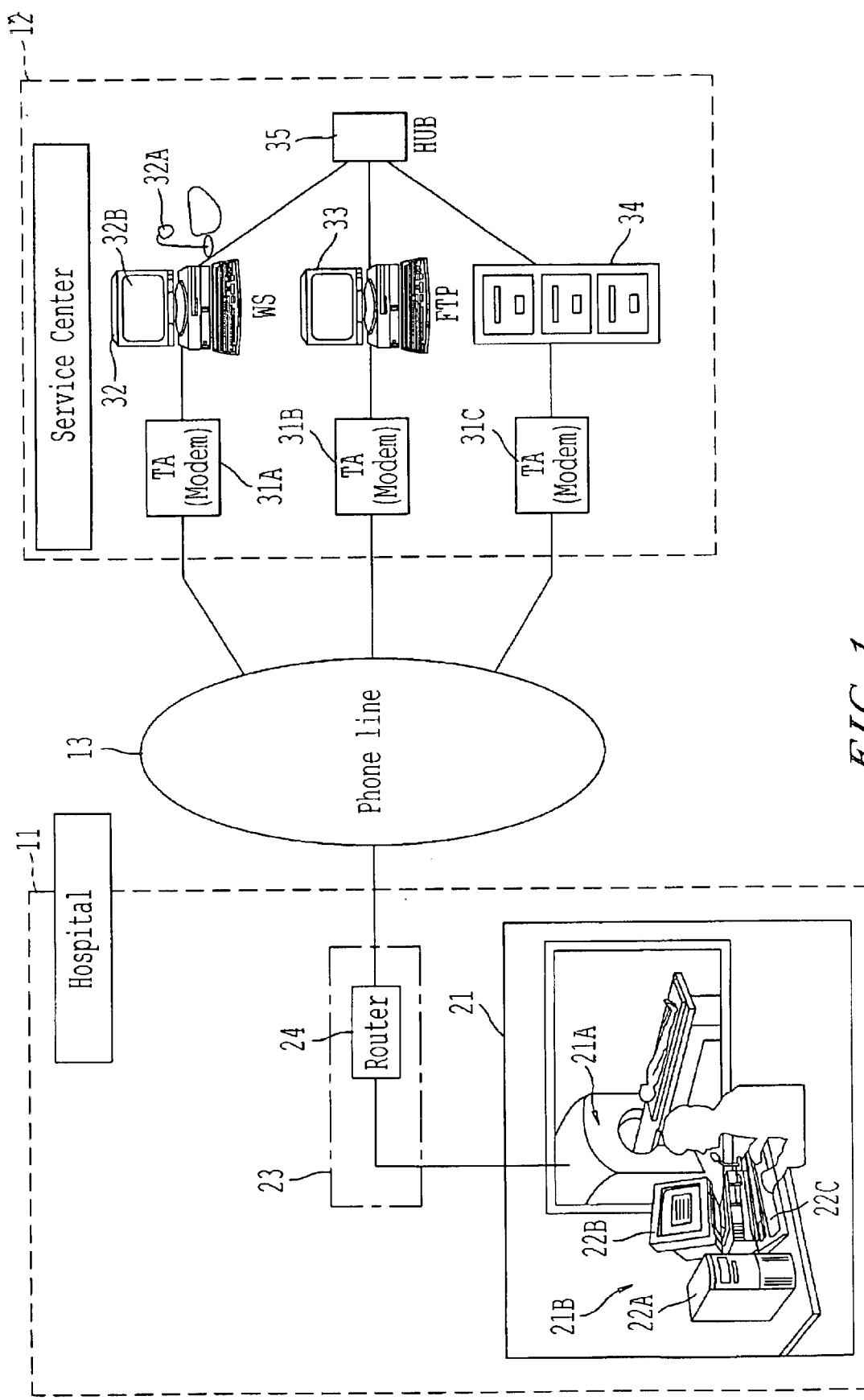
FIG. 1 is a block diagram showing the remote maintenance and operating guidance system according to one embodiment of the present invention.

Referring now to the drawings, wherein like reference numerals designate identical or corresponding parts throughout the several views, and more particularly to FIG. 1 thereof, FIG. 1 illustrates an outline configuration of a remote maintenance and operating guidance system whereby the maintenance and operation of medical equipment in a hospital or other medical facility are guided from a remote location. This remote maintenance and operating guidance system functionally includes the operating guidance system to which the present embodiment pertains, it being understood that in this context the expression 'remote location' signifies physical separation from the medical equipment. This may refer to a location outside the hospital itself, or to a room within the hospital which is different from the room in which the medical equipment is located. Similarly, the expression 'operating guidance' is to be taken to signify not only guidance in relation to the operation of the equipment as such, but also training and surrogate operation.

In outline this remote maintenance and operating guidance system is configured in such a way that a hospital 11 (medical facility) and a service center 12 (service facility) are joined by means of a dedicated telephone line 13 in such a manner as to be able to communicate with each other.

It should be noted that in this context 'service center' signifies a facility which supplies various services relating to the maintenance and operation of medical equipment. The facility may be known by a variety of names including 'service station,' 'maintenance center,' 'control center,' 'base control center' and 'technical assistance center.' Moreover, the cost of this remote maintenance and operating guidance center may be included in the fee stipulated in a contract concluded in advance between the hospital 11 and the service center 12, or may be payable prorate in accordance with the frequency and duration of operating guidance.

The medical system 21 is located in a specified room within the hospital 11, and includes a large-scale imaging modality including magnetic resonance imaging, X-ray CT scanning, X-ray diagnostic, nuclear medicine imaging, ultrasonic calculus pulverizing, SQUID and ultrasonic diagnostic devices.

The medical system 21 has a medical equipment (gantry, bed etc.) 21A and an operating device 21B from which the operator operates the medical equipment 21A. The operating device 21B includes a computer 22 (main unit 22A, monitor 22B, console 22C etc.). The function of the computer 22 is to determine the filming conditions interactively with the operator, and transmit these conditions to the medical equipment 21A.

Figure 2:
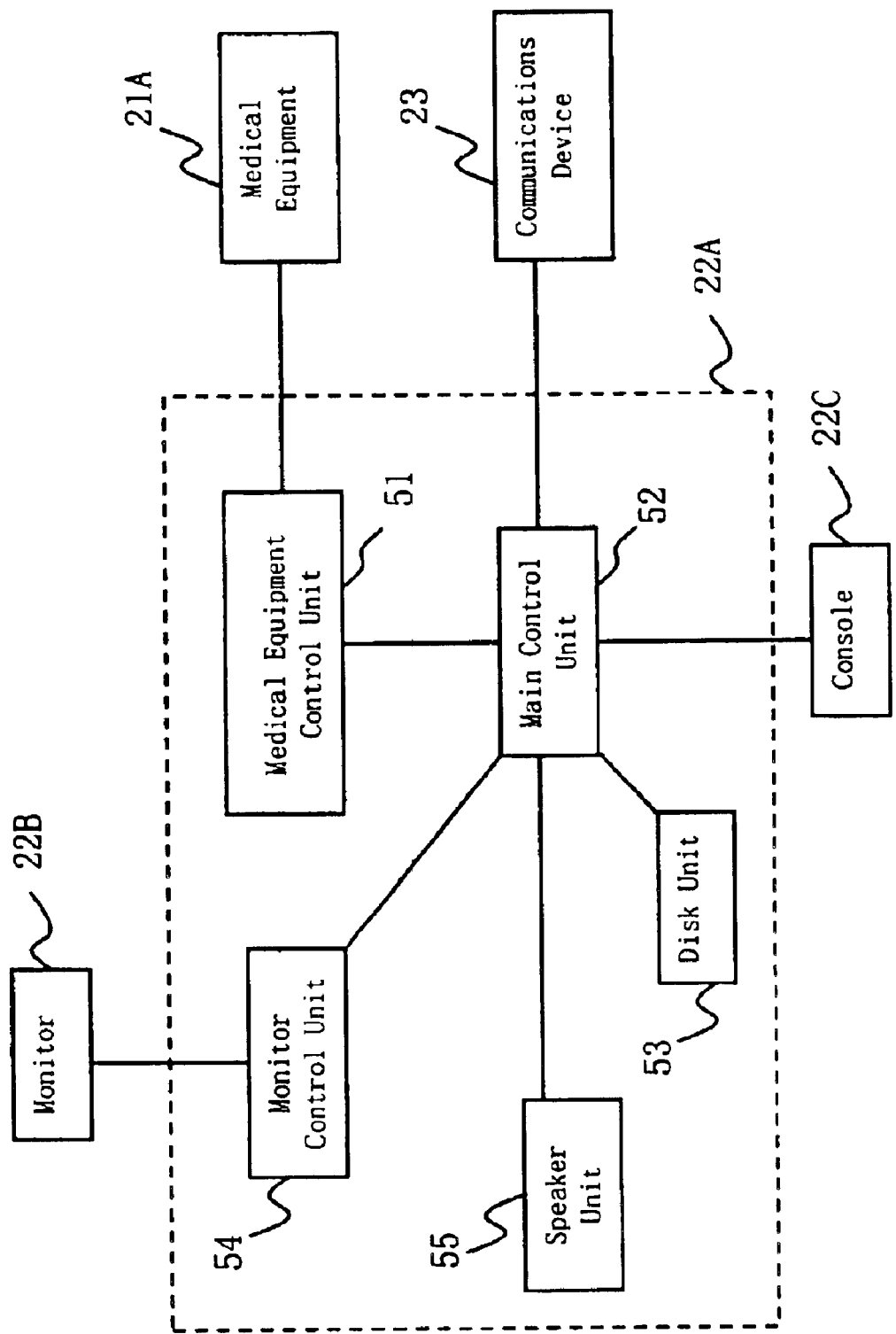
FIG. 2 is a block diagram showing an operating device according to an embodiment of the present invention.

FIG. 2 is a block diagram showing the computer 22. The computer 22 includes a medical equipment control unit 51 which controls a medical equipment 21A, a monitor control unit 54 which controls the monitor 22B, a speaker unit 55 which outputs a sound, a disk unit 53 in which the elapsed time, described below, and other programs and data are stored in and a main control unit 52 which controls the above units. The main control unit 52 is electrically connected to the console 22C.

Another function of the computer 22 is to collect and store data relating to the state of operation of the medical equipment 21A, this being achieved by running a diagnostic program which has been stored in advance. Thanks to this facility, data relating to the present and past states of operation of the medical equipment 21A is always stored in the computer 22. Moreover, as will be explained below, the computer 22 is also equipped with a program which serves to process operating guidance (including operational training) between it and the service center 12. The monitor 22B and console 22C also function as a man-machine interface between the medical system 21 and the remote maintenance and operating guidance system.

Meanwhile, a communications device 23 is provided in the hospital 11 for the purpose of transmitting and receiving images and sounds (voice). This communications device 23 is connected to the medical system 21, and contains a router 24 which is connected to the aforesaid dedicated telephone line 13 in such a manner as to permit communications.

The dedicated telephone line 13 may be a consolidated digital communications network, or may be a communications network such as the Internet. It may assume the form of a LAN (local are a network) or WAN (wide area network).

A server system in the service center 12 is equipped with terminal adapters (TA) or modems 31A–31C connected to the dedicated telephone line 13. To each of these terminal adapters is connected a work station 32, FTP (file transfer protocol) server 33 and file server 34. The work station and servers are connected by means of a hub 35. The work station 32 is equipped with a microphone 32A and a monitor 32B.

Dedicated maintenance control and operating guidance staff are permanently stationed in the service center 12. If the staff specialist receives notification of a fault or other problem from the hospital 11, he can access the computer 22 in the hospital 11 directly on-line from the work station 32 by way of the dedicated telephone line 13. In this manner the staff specialist can diagnose the fault on the basis of performance data on the main unit 1 detected and stored in the computer 22, and if necessary can run a diagnostic program on the computer 22 and collect data.

The staff specialist in the service center 12 or another experienced operator can respond remotely by way of the work station 32 to requests for operating guidance (including operational training) from the hospital 11.

The following describes the processes involved in remote operating guidance. Firstly, the five guidance modes will be explained. Guidance modes 1–5 are provided under the remote maintenance and operating guidance system to which the present embodiment pertains.

In guidance mode 1, a staff specialist in the service center monitors the performance of the medical equipment on the monitor 32B in the hospital and provides advice on its actual operation by voice. In this guidance mode, the same image is displayed on the monitor 32B of the work station 32 and the monitor 22B of the operating device 21B in the hospital 11. The image displayed depends on the diagnostic or guidance program which is installed in the work station 32. In other words, the image displayed on the monitor 22B is transmitted from the hospital 11 to the service center 12 and the staff specialist in the service center 12 can see simultaneously the same image which the operator in the hospital 11 sees although they are physically remote. This means that the staff specialist can give the necessary guidance by voice instructions while viewing his own monitor screen. In this manner the operator in the hospital 11 can receive operating guidance by voice from the staff specialist in the service center 12.

In guidance mode 2, the staff specialist in the service center 12 remotely operate the medical system 21 in the hospital 11 by way of the work station 32. This allows the staff specialist to demonstrate details of the operation to the operator sitting in front of the operating device 21B through the monitor screen while giving voice instructions. This on-screen guidance (for instance, moving the cursor) is displayed simultaneously on the monitor 22B controlled by the monitor control unit 54 in the hospital 11, while the voice of the staff specialist is broadcast through the internal speaker unit 55 of the computer 22. Detailed guidance on filming conditions and other factors given in guidance mode 2 can be stored automatically by the operating device 21B or the file server 34 at a command from the operator in the hospital 11 or the specialist staff in the service center 12.

In guidance mode 3, the staff specialist in the service center 12 remotely determines filming conditions and other factors of the medical equipment 21A controlled by the medical equipment control unit 51 in the hospital 11, so that the operator in the hospital 11 can immediately begin filming.

Guidance mode 4 is a development of guidance mode 2 and allows the operator in the hospital 11 to replay details of the guidance received in guidance mode 2 so that he may check and revise it. In other words, the voice of the staff and the operation demonstrated by the staff which have been stored in the disk unit 53 are loaded then outputted from the speaker unit 55 and displayed on the monitor 22B, respectively.

In guidance mode 5, operational instruction files and voice files stored in advance in FTP server 33 of the service center 12 are transmitted to the operating device 21B in the hospital 11. The files may, for instance, be stored in the disk unit 53 so that the operator in the hospital 11 may check and revise their content.

Figure 3:
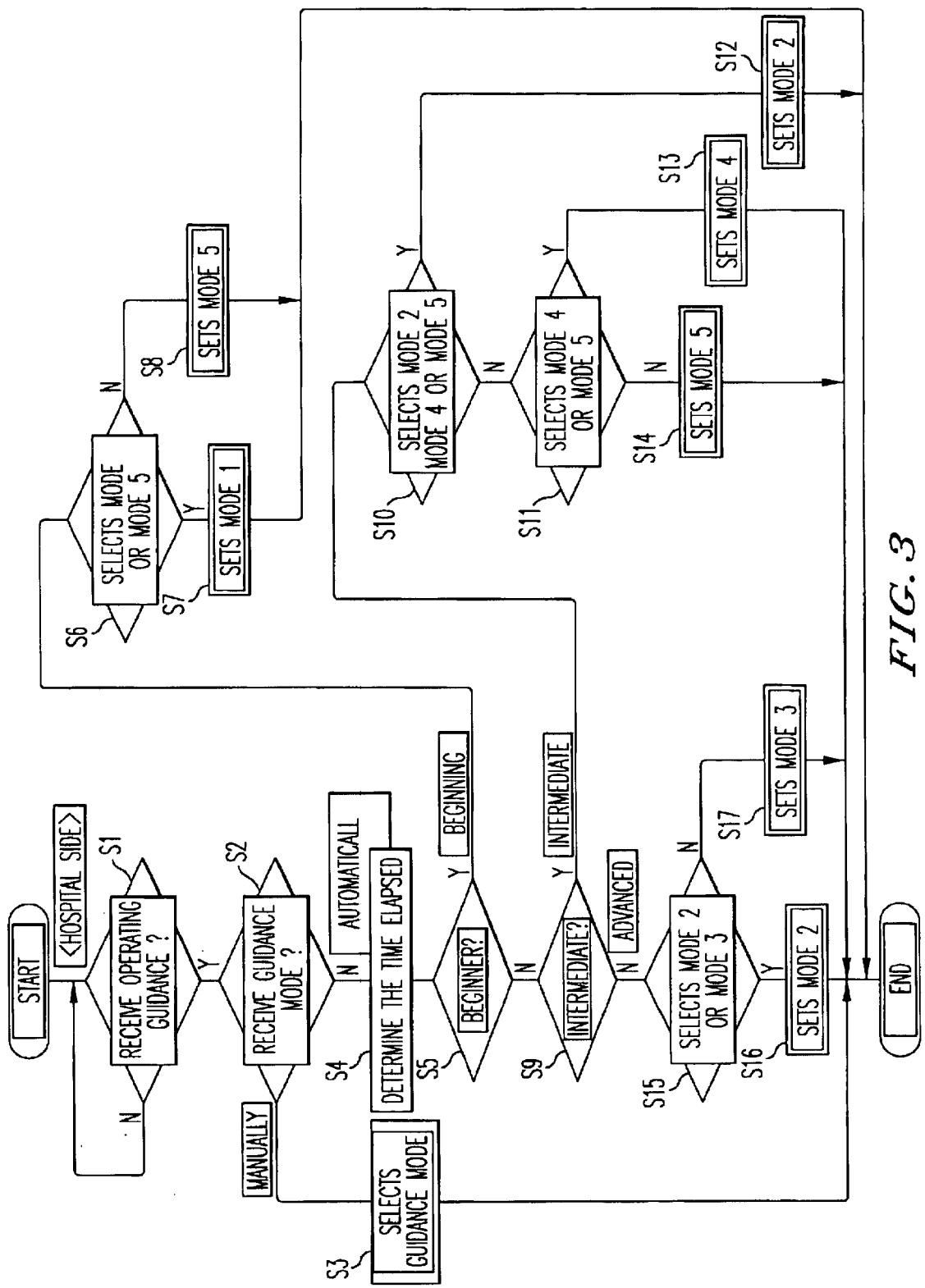
FIG. 3 is a flow chart showing the process of selecting the guidance mode as implemented by a hospital; according to an embodiment of the present invention
Figure 4:
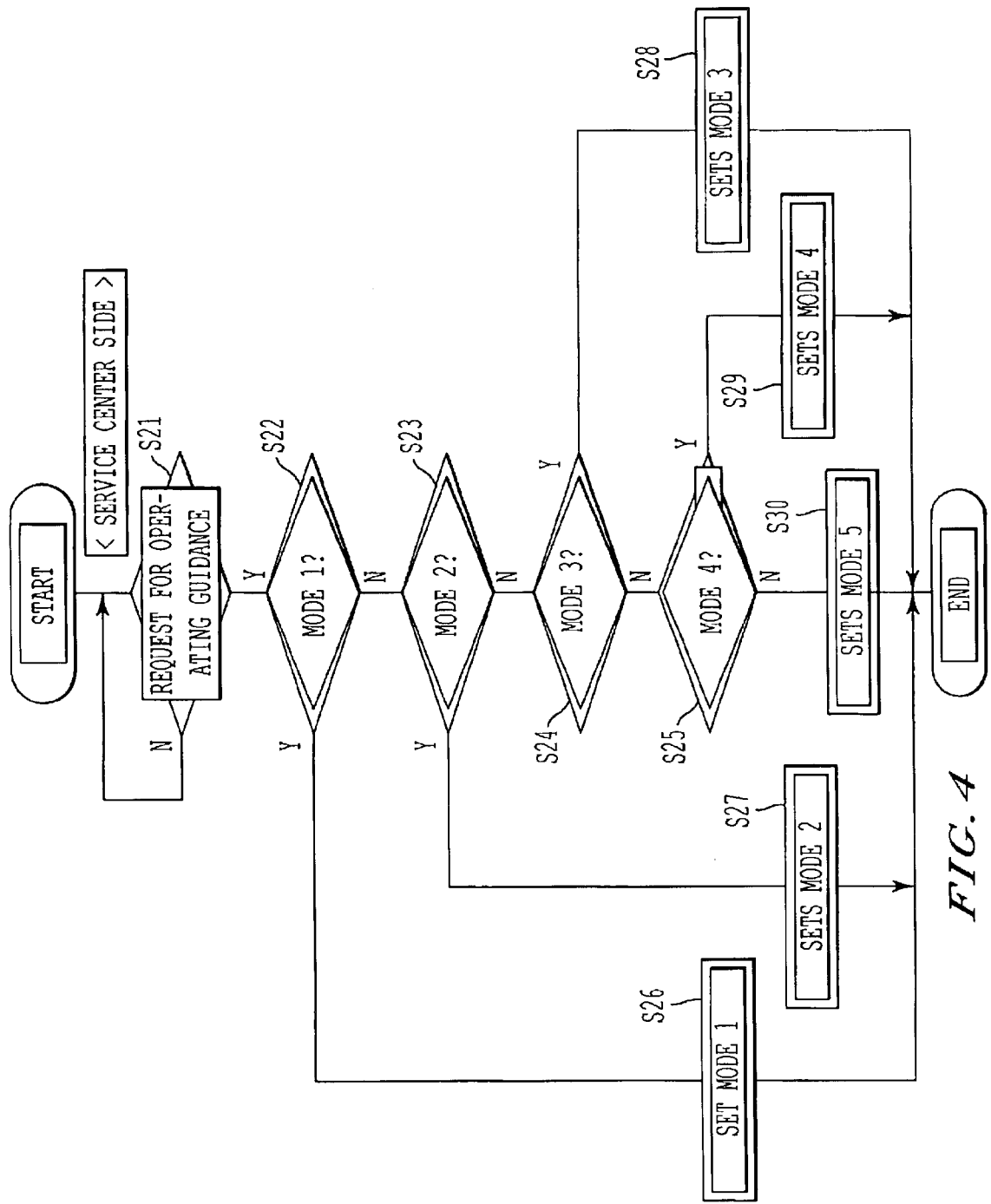
FIG. 4 is a flow chart showing the process of setting up the guidance mode as implemented by a service center according to an embodiment of the present invention.

Guidance modes 1–5 can be selected and set automatically to match the experience of the operator in the hospital 11. FIGS. 2 and 3 illustrate the outline process involved in this automatic selection and setting. FIG. 3 illustrates the process as performed on the operating device 21B in the hospital 11, while FIG. 4 illustrates the process performed on the work station 32 in the service center 12 in response to that in FIG. 3.

As shown in FIG. 3, the operating device 21B decides at a command from the operator whether or not to receive operating guidance (Step 1). If the answer is YES (receive operating guidance), it decides as an option whether to receive a guidance mode manually (Step 2). If the answer is YES, the operator selects his desired guidance mode from among modes 1–5 (Step 3). In this manner, the mode is selected and set according to the needs of the operator.

Meanwhile, if the answer at Step 2 is NO, the operating device 21B recognizes that the instruction for automatic selection and setting has been given. In this case the operating device 21B now determines the elapsed time of the medical system 21. The expression 'elapsed time' signifies the time elapsed since a predetermined time, which may be the time since the introduction of the medical system 21 or the time since installation of a program in the medical system 21, for example. This elapsed time provides one parameter for inferring the experience of the operator, and is controlled by the memory of the operating device 21B or the service center 12. In other words, it is generally assumed that the experience of the operator is in direct proportion to the length of time elapsed.

However, since operators may change, it is also possible for the operator manually to select the relevant grade of experience (beginner, intermediate, advanced), as explained below. The parameter used for automatic selection may be the frequency of filming or an identification code of the medical equipment 21A instead of the time elapsed. The parameter may be determined according to the operator of the medical equipment. This parameter is a working term of the operator or a division of the operator (surgery, internal medicine), for example. Moreover the parameter may be determined according to a sort of disease of the patient, for example, cardiac infarction or brain cancer. Not only the operator but also the staff can rewrite the parameter from the server system in service center 12.

Once the assessment of time elapsed is complete in Step 4, the operating device 21B assesses whether the operator is beginner grade (not long since the medical equipment was introduced) (Step 5). If the answer is YES, the guidance mode 1 and guidance mode 5 are automatically selected and displayed on the monitor 22B. The operator can select guidance mode 1 or guidance mode 5 (Step 6) with the console 22C. In accordance with the result of this selection, either guidance mode 1 or guidance mode 5 is set (Steps 7 and 8).

If the answer at Step 5 is NO, and the operator is assessed not to be beginner grade, he is then assessed for intermediate grade (Step 9). If the answer is YES and he is recognized as intermediate grade, the guidance mode 2, guidance mode 4 and guidance mode 5 are automatically selected and displayed on the monitor 22B. The operator can select guidance mode 2, guidance mode 4 or guidance mode 5 (Steps 10 and 11). In accordance with the result of this selection, either guidance mode 2, 4 or 5 is set (Steps 12–14).

If the answer at Step 9 is NO, it is assumed that a fair amount of time has elapsed since the introduction of the medical equipment, and the operator is assessed as advanced grade. In this case the operator can select guidance mode 2 or guidance mode 3. Depending on the result of this selection, either guidance mode 2 or guidance mode 3 is set (Steps 15–17).

Meanwhile, as may be seen from FIG. 4, the work station 32 in the service center 12 is monitoring to see whether there will be a request for operating guidance from the hospital 11 (Step 21). If there is a request, the work station 32 assesses which of the guidance modes 1–5 is required (Steps 22–25). Depending on the result of this assessment, one of the guidance modes 1–5 is set up (Steps 26–30).

Thus, the work station 32 implements operating guidance to the operating device 21B in the hospital 11 in accordance with the selected guidance mode.

In this manner the present embodiment allows operating guidance to be given from a remote location to the operator of medical system 21 in a hospital 11 in accordance with the operator's experience.

More specifically, if the medical system 21 has been introduced recently and the operator is beginner grade, he can receive voice instructions from a staff specialist who is watching the same operational screen in the service center (guidance mode 1). Guidance can be given either during actual filming or as an exercise in operating the equipment.

It is also possible to practice by replaying operational instruction files and voice files stored in the service center 12 on the console of the operating device 21B (guidance mode 5). This allows the operator to practice comparatively simple operations when he has time and at his own pace.

When the operator graduates from beginner grade to intermediate grade, he can watch remote guidance with voice (guidance mode 2), replay and check recorded data (guidance mode 4), and replay operational instruction files and voice files stored in the service center 12 on the operating device 21B (guidance mode 5).

This allows him to learn details which are not covered in the files he used as a beginner or in the instruction manual through question and answer sessions with the staff specialist in the service center 12. Moreover, it is also possible for the staff specialist in the service center 12 to watch the operations performed by the operator from a distance or to operate the console by remote control, so that the operator can observe and learn from this. Moreover, the operator can replay pre-recorded operational instruction files and voice files, practicing until he is confident and thus improving the level of his experience.

As time elapses from the introduction of the medical equipment, the operator is assumed to have reached advanced level, and the guidance mode is automatically set in accordance with this. In other words, in addition to remote operation and observation of the medical equipment and voice instruction from the service center 12 (guidance mode 2), it also becomes possible to set filming conditions and other factors (guidance mode 3).

In this manner the staff specialist in the service center 12 can respond to requests by the operator and give advice on the collection of clearer clinical images in accordance with data relating to clinical cases and experience in other universities and the characteristics of the medical system 21.

It is also possible for the staff specialist to operate the imaging parameters of the medical system 21 from a distance, so that through a process of trial and error in advanced-stage operations between the operator in the hospital 11 and the staff specialist in the service center 12 the latter can provide more advanced operational aid.

In this manner according to the present embodiment the operator in the hospital 11 who is receiving remote operating guidance from the staff specialist can either select at will his desired guidance mode or allow it to be set automatically in accordance with his experience. This means that not only is it possible to communicate operational details accurately to the operator, but trouble stemming from lack of understanding on the part of the operator can be prevented. Especially where a considerable gap exists between understanding and experience of operation on the part of the parties giving and receiving guidance, it is possible to select the optimal guidance mode, allowing the necessary guidance or training to be implemented.

Figure 5:
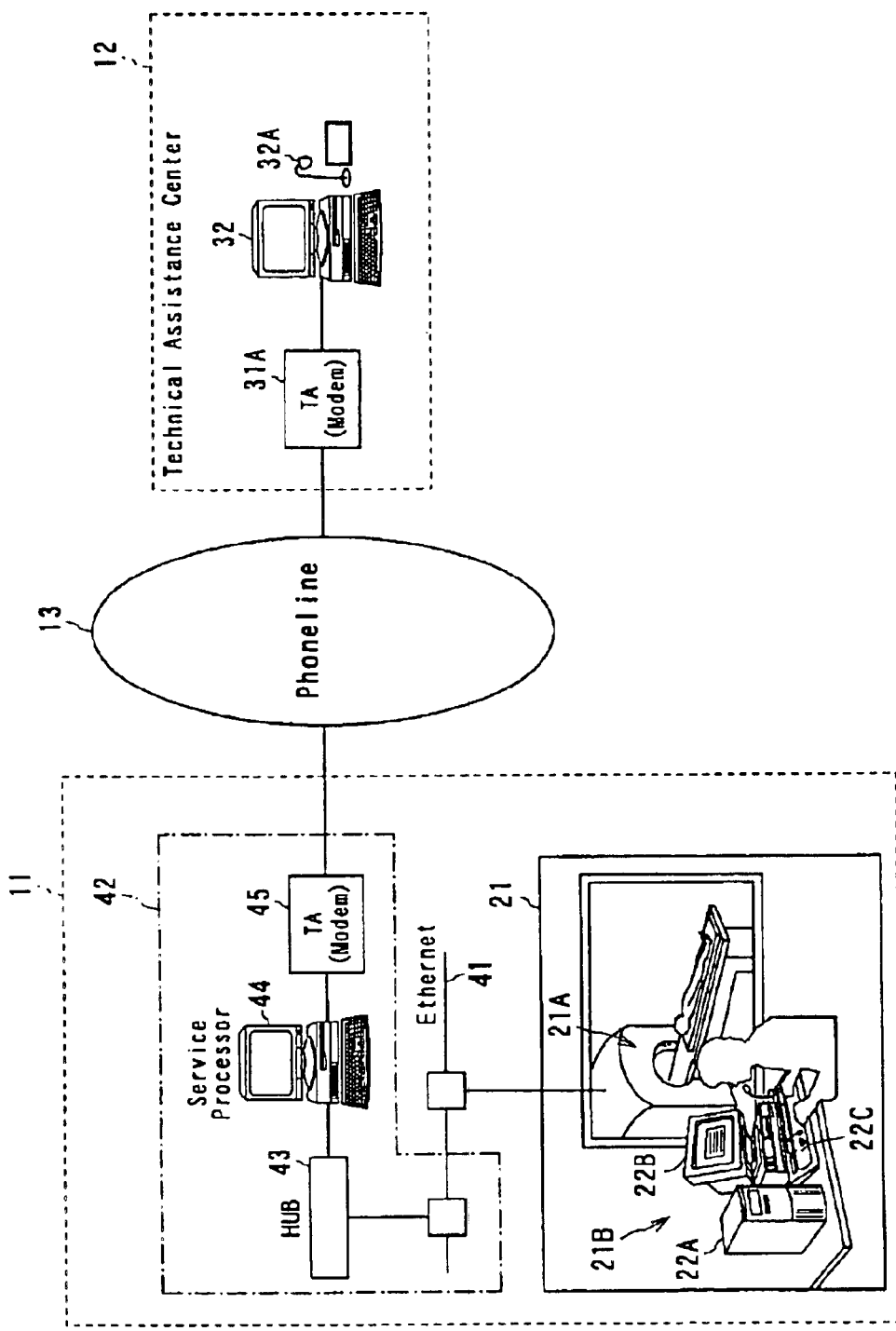
FIG. 5 is a block diagram showing the outline structure of the remote maintenance and operating guidance system according to another embodiment of the present invention.

It should be added that the remote maintenance and operating guidance system to which the present invention pertains is in no way restricted to the configuration illustrated in FIG. 1, and a configuration such as illustrated in FIG. 5 may also be adopted. This system offers only remote operating guidance, and not remote maintenance.

That is to say, in the system illustrated in FIG. 5 the hospital 11 has an internal LAN 41, to which the medical system 21 is connected. A control and communications system 42 is also connected to the LAN 41. This control and communications system 42 has a hub 43 connected to the LAN 41, a service processor 44 connected to this hub and serving to store and display files, and a terminal adapter (or modem) 45. The processor 44 works in conjunction with the service center 12, processing the guidance modes 1–5 on the hospital side. The terminal adapter (or modem) 45 is connected by way of the dedicated telephone line 13 to the work station 32 in the service center 12. This configuration is capable of producing the same effect as the previous embodiment.

As has been described above, the operating guidance system for medical equipment to which the present invention pertains makes it possible to transmit details of the method of operation of the medical equipment more accurately and effectively to the operator from a location remote from the medical equipment, allowing operational problems to be avoided in advance and proving very effective for use in learning and gaining experience in the operation of large-scale modalities, the operation of which is becoming increasingly complex in recent times.

The above is a description of embodiments of the present invention, which is nevertheless in no way restricted to the configurations described therein, and may be changed or modified as suitable provided that it does not diverge from the gist of the invention as described in the claims, such configurations also being included within the scope of the present invention.

What is claimed as new and desired to be secured by letters patent of united states is:

1. A medical system located in medical facility and connected via a communication network to a server system in a service center located at a distance from the medical facility, comprising:

a disk unit configured to store a plurality of ways an operator can be guided in an operation of the medical system;

a selection unit configured to select automatically at least one of the ways based on a parameter for selection stored in the disk unit;

a monitor control unit configured to display the selected way on a monitor of the medical system;

a console with which the operator selects at least one of the ways displayed on the monitor; and a communications device which interchanges data with the service center according to the selected way.

2. The medical system according to claim 1, wherein the parameter for selection is rewritable from the service center.

3. The medical system according to claim 1, wherein the parameter for selection is related to an elapsed time of the medical system.

4. The medical system according to claim 1, wherein the parameter for selection is related to the frequency of filming with the medical system.

5. The medical system according to claim 1, wherein the parameter for selection is related to a model number of the medical system.

6. The medical system according to claim 1, wherein the parameter for selection is related to a sort of disease of a patient filmed with the medical system.

7. The medical system according to claim 1, wherein the parameter for selection is related to an operator who operates the medical system.

8. The medical system according to claim 7, wherein the parameter for selection is related to a division to which the operator belongs.

9. The medical system according to claim 7, wherein the parameter for selection is related to a working term of the operator.

* * * * *